United States Patent
Bianchi et al.

(10) Patent No.: US 11,648,252 B2
(45) Date of Patent: May 16, 2023

(54) METHOTREXATE FOR USE AS A MEDICAMENT

(71) Applicant: GF SERVICE S.R.L., Assago (IT)

(72) Inventors: Federica Bianchi, Genoa (IT); Maria Giovanna Bianchi, Genoa (IT)

(73) Assignee: GF SERVICE S.R.L., Assago (IT)

( * ) Notice: Subject to any disclaimer, the term of this patent is extended or adjusted under 35 U.S.C. 154(b) by 164 days.

(21) Appl. No.: 17/050,592

(22) PCT Filed: Apr. 24, 2019

(86) PCT No.: PCT/EP2019/060468
§ 371 (c)(1),
(2) Date: Oct. 26, 2020

(87) PCT Pub. No.: WO2019/206966
PCT Pub. Date: Oct. 31, 2019

(65) Prior Publication Data
US 2021/0121464 A1    Apr. 29, 2021

(30) Foreign Application Priority Data

Apr. 27, 2018 (IT) .......... 102018000004922

(51) Int. Cl.
*A61K 31/519* (2006.01)
*A61P 19/02* (2006.01)
*A61K 9/00* (2006.01)

(52) U.S. Cl.
CPC .......... *A61K 31/519* (2013.01); *A61K 9/0019* (2013.01); *A61P 19/02* (2018.01)

(58) Field of Classification Search
CPC . H01L 29/1033; H01L 29/16; H01L 29/1604; H01L 29/36; H01L 29/42376; H01L 29/66795; H01L 29/785; H01L 29/7851; H01L 29/7853
See application file for complete search history.

(56) References Cited

FOREIGN PATENT DOCUMENTS

WO        2014164299 A1    10/2014

OTHER PUBLICATIONS

Jin Wen, Neuropharmacology, Sep. 1, 2018;139:76-84 (Year: 2018).*
Huw Richard H R Davies, Cochrane Database Syst Rev. Jul. 1998; 1998(3) teaches (Year: 1998).*
Anna O'connor et al, "The rapid kinetics of optimal treatment with subcutaneous methotrexate in early inflammatory arthritis: an observational study", BMC Musculoskeletal Disorders,vol. 17, No. 1, Aug. 24, 2016, pp. 1-7.
Bianchi G. et al, "Methotrexate and Rheumatoid Arthritis: Current Evidence Regarding Subcutaneous Versus Oral Routes of Administration", Adv Ther. Feb. 4, 2016 (Feb. 4, 2016), vol. 33, No. 3, p. 369-378.
Bianchi G., "Step-Down Methotrexate Therapy in Rheumatoid Arthritis (Stemetra): A Pilot Study to Assess the Safety and The Tolerability of High-Dose Methotrexate", Jun. 12, 2018 (Jun. 12, 2018), Annals of the Rheumatic Diseases, p. 975,Retrieved from the Internet:URL:https://ard.bmj.com/content/annrheumdis/77/Suppl_2/975.1.full.pdf.
Gabriel S., et al., "Treatment of rheumatoid arthritis with higher dose intravenous methotrexate",The Journal of Rheumatology, 1990; 17-4, pp. 460-465.
Robert M. Michaels et al, "Weekly intravenous methotrexate in the treatment of rheumatoid arthritis", Arthritis & Rheumatism,vol. 25, No. 3, Mar. 1, 1982, p. 339-341.
Search Report and Written Opinion of PCT/EP2019/060468 dated Jul. 17, 2019.

* cited by examiner

Primary Examiner — Jean P Cornet
(74) Attorney, Agent, or Firm — Silvia Salvadori, P.C.; Silvia Salvadori

(57) ABSTRACT

The present invention relates to methotrexate, a pharmaceutically acceptable salt thereof, or a hydrate thereof, for use as a medicament, characterized in that methotrexate, a pharmaceutically acceptable salt, or a hydrate thereof is administered at a dose which is decreased within a treatment time comprising at least two subsequent sequential time periods in the form of a first and a second time period, each time period comprising at least one week, wherein the dose administered in the second time period is lower than that of the first time period, with the proviso that within the total treatment time, the average dose of methotrexate, a pharmaceutically acceptable salt there of, or a hydrate thereof administered is at least 20 mg/week.

8 Claims, 1 Drawing Sheet

METHOTREXATE FOR USE AS A MEDICAMENT

This application is a U.S. national stage of PCT/IB2019/060468 filed on 24 Apr. 2019, which claims priority to and the benefit of Italian Patent Application No. 102018000004922 filed on 27 Apr. 2018, the contents of which are incorporated herein by reference in their entireties.

FIELD OF THE INVENTION

The present invention relates to methotrexate, a pharmaceutically acceptable salt thereof, or a hydrate thereof, for use as a medicament, wherein methotrexate, a pharmaceutically acceptable salt thereof, or a hydrate thereof is administered by means of a specific dosage regime.

BACKGROUND OF THE INVENTION

Methotrexate (MTX) is at present the drug of first choice in treating rheumatoid arthritis (RA) with an efficacy rate, as a monotherapy, of about 35%. The efficacy of MTX therapy may increase if combined with anti-TNF biologics drugs. This treatment option, however, due to the high cost of biologics and their side effects, is considered a second choice, suggested for patients with a severe disease or with poor prognosis or who do not respond adequately to treatment with MTX monotherapy. For these reasons, any study investigating new therapeutic approaches that can improve the efficacy of MTX seems useful.

It is known that the modality of administration of MTX, i.e. dose and route of administration, may influence the efficacy of therapy. The use of subcutaneous (SC) MTX is, in fact, better tolerated and more effective than oral (OR) MTX at the same dosage. The effectiveness of MTX is dose-dependent, either alone or in combination with anti-TNF drugs, with a dose generally ranging from 7.5 mg/week to 25 mg/week.

Up to now, a MTX dosage higher than 25 mg was tested only occasionally in small groups of patients, but with good tolerability and efficacy, as derivable from the following publications:

Michaels et al., "*Weekly intravenous methotrexate in the treatment of rheumatoid arthritis*", Arthritis and Rheumatism, 1982, 25 (3), pages 339 to 341 discloses a MTX intravenous (IV) dosage of 50 mg/week for 2 to 20 weeks. 35% of the 14 test persons had to reduce or discontinue the treatment due to toxicity in the form of oral ulceration, GI symptoms and liver enzyme abnormalities.

Gabriel S., et al., "*Treatment of rheumatoid arthritis with higher dose intravenous methotrexate*", J. Rheumatol, 1990, 17, pages 460 to 465 discloses a MTX IV dosage by means of a body surface area (BSA) based dosing with an initial dose of 40 mg/m$^2$ and a final dose of 26 mg/m$^2$. However, due to discontinued MTX dosage in case of patient's tolerability problems, the maximum mean dose of 10.5 mg/week achieved over the treatment period was quite low. Two of the 10 test persons did not complete the study due to infected plantar or severe nausea.

Shiroky J. B. et al., "*High dose intravenous methotrexate for refractory rheumatoid arthritis*", J. Rheumatol. 1992 February, 19(2), pages 247 to 251 discloses IV dosage of 500 mg/m$^2$ for a treatment time of 24 weeks, and in addition 25 mg/m$^2$ oral administration of folinic acid within 24 hours after MTX dosage. 37% of the 8 test persons withdrew the treatment due to inefficacy, GI intolerance or sciatica.

Furst D. E. et al., "*Increasing methotrexate effect with increasing dose in the treatment of resistant rheumatoid arthritis*", J. Rheumatol., 1989, 16, pages 313 to 320 discloses an MTX dosage regime with oral administration, in which the dosage is increased from 5 mg/m$^2$ to 10 mg/m$^2$ to 15 mg/m$^2$ within a treatment time of 16 weeks. 33% of the 36 test persons discontinued the treatment due to high toxicity.

Lambert C. M. et al., "*Dose escalation of parenteral methotrexate in active rheumatoid arthritis that has been unresponsive to conventional doses of methotrexate: a randomized, controlled trial*", Arthritis Rheum., 2004, February, 50(2), pages 364 to 371 discloses an MTX dosage regime with intramuscular administration, in which the dosage is increased from 15 mg/m$^2$ to 20 mg/m$^2$ to 25 mg/m$^2$ to 35 mg/m$^2$ to 45 mg/m$^2$ within a treatment time of 22 weeks. In addition to MTX, 5 mg folinic acid was administered per week within 24 hours after the MTX dosage. 18.5% of the 27 test persons discontinued the treatment due to recurrent chest infections or inefficacy of the treatment.

The recent meta-analysis of Bergstra S. A. et al., "*Meta-Regression of a Dose-Response Relationship of Methotrexate in Mono-and Combination Therapy in Disease-Modifying Antirheumatic Drug-Naive Early Rheumatoid Arthritis Patients*", Arthritis Care Res (Hoboken), 2017, October,69 (10):1473-1483 suggests that starting with higher doses of MTX doesn't improve outcomes. However, the results of this study are severely hampered by the fact that only one study with subcutaneous (SC) MTX was considered and, since the oral absorption of MTX starts to plateau at a dosage of 15 mg/week, these findings could not be generalized, as discussed in Schiff M. H. et al., "*Head-to-head, randomised, crossover study of oral versus subcutaneous methotrexate in patients with rheumatoid arthritis: drug-exposure limitations of oral methotrexate at doses≥15 mg may be overcome with subcutaneous administration*", Ann Rheum Dis., 2014, August, 73(8), pages 1549 to 1551.

WO 2014/164299 A1 relates to a method of treating an autoimmune disorder in a patient in need thereof comprising administering to the patient an effective amount of a combination of levocetirizine and montelukast. In addition to this combination, MTX might be administered.

T. Y. WOO et al., "*Cutaneous lesions of dermatomyositis are improved by hydroxychloroquine*", Journal of the American Academy of Dermatology, Mosby Inc., US, vol. 10, no. 4, 1. Jan. 1984 (1984-01-01), pages 592-600, discloses a study wherein the effectiveness of hydroxychloroquine is tested on persons having dermatomyositis.

S. Din et al., "*Use of methotrexate in refractory Crohn's disease: The Edinburgh experience*", Inflammatory Bowel Diseases, vol. 14, no. 6, 1 Jun. 2008 (2008-06-01), pages 756-762, discloses a study in which the use of MTX as immunosuppressant was tested for the treatment of Crohn's disease.

G. Bianchi et al., "*Methotrexate and Rheumatoid Arthritis: Current Evidence Regarding Subcutaneous Versus Oral Routes of Administration*", Advances in therapy, Health Communications, Metuchen, vol. 33, no. 3, 4 Feb. 2016, pages 369-378, is a scientific review article summarizing the state of the art in the field of use of MTX for the treatment of rheumatoid arthritis.

A. O'Connor et al., "*The rapid kinetics of optimal treatment with subcutaneous methotrexate in early inflammatory arthritis: an observational study*", BMC Musculoskeletal Disorders, vol. 17, no. 1, 24, Aug. 2016, pages 1 to 7, discloses a study relating to subcutaneous MTX dosing for treating rheumatoid arthritis, with the objective to determine rapidity of response of subcutaneous MTX in early rheumatoid arthritis.

MTX is a prodrug producing anti-arthritic effects through a folylpolyglutamate synthase activation to MTX polyglutamates (MTX-PGs). The selective emergence of long-chain MTX-PGs is related to the dose, the time of exposure and hence to the dosage intensity of MTX, and it appears that the accumulation of MTX-PGs is an important determinant of response to MTX treatment. Consequently, the intensity of MTX administration, that is dose, duration, and route of administration determines the effect of the accumulation of MTX-PGs.

Therefore, theoretically, it would make mechanistic sense to start with a relatively high MTX dose and administer it subcutaneously, because subcutaneous administration appears to be superior in view of pharmacokinetics compared with other administration routes like oral, intravenous or intramuscular. However, hitherto, relatively high MTX doses were not applied, because it is well known that relatively high MTX doses result in more severe side effects.

Hence, in view of the known MTX dosages and administration regimes thereof, there is a need for an improved MTX dosage for treating diseases, in particular rheumatic and/or inflammatory diseases, and most particularly rheumatic arthritis.

OBJECT OF THE INVENTION

It is the object of the present invention to provide a medical use of MTX which provides an efficient relief of the patient from the disease to be treated, while tolerability is at least not negatively changed or even improved compared to prior art MTX dosing.

In particular, it was surprisingly found by the present inventors that MTX dosing can be started with a relatively high dose, and then be stepwise decreased. For the stepwise decrease, attention has to be paid to the average dose of MTX, a pharmaceutically acceptable salt thereof, or a hydrate thereof, administered to a patient during the treatment time. This is surprising all the more since prior MTX dosage regimes typically start with a relatively low MTX dosing in view of the well known tolerability problems with relatively high MTX doses.

Hence, owing to the present inventive concept of a medical use of MTX, a pharmaceutically acceptable salt thereof, or a hydrate thereof, with an administration by a specific dosage regime, a medical use of MTX is provided which is significantly improved to prior art MTX dosage.

DESCRIPTION OF THE INVENTION

The aforementioned object is achieved by the present invention by means of methotrexate, a pharmaceutically acceptable salt thereof, or a hydrate thereof, for use as a medicament.

The methotrexate, a pharmaceutically acceptable salt thereof, or a hydrate thereof, is subcutaneously administered at a dose which is decreased within a treatment time comprising at least two subsequent sequential time periods in the form of a first and a second time period, each time period comprising at least one week, wherein the dose administered in the second time period is lower than that of the first time period. Namely, the aforementioned dosage regime is as follows:

i) within a first time period, the dose is 38 to 80 mg/week;

ii) within a second time period, the dose is 22 to 34 mg/week; and iii) within a third time period, the dose is 8 to 20 mg/week, the duration of each of the first, second and third time period is at least two weeks respectively, and the first, second and third time period subsequently follow in direct succession.

This dosage regime is applied with the proviso that within the total treatment time, the average dose of methotrexate, a pharmaceutically acceptable salt thereof, or a hydrate thereof administered is 26 to 40 mg/week.

The term "methotrexate" as used herein means the organic compound having the Chemical Abstracts (CAS) registry number 59-05-2 and the IUPAC name (2S)-2-[[4-[(2,4-diaminopteridin-6-yl)methyl-methylamino]benzoyl]amino]-pentanedioic acid. In the following, the term "methotrexate" may be abbreviated as MTX.

Here and in the following, for the terms "is administered" and "administered", likewise, the term "for administration" may be used as synonym. Because, with the present medical use, no treatment of the human or animal body by surgery or therapy and diagnostic methods practiced on the human or animal body is intended.

The term "pharmaceutically acceptable salt thereof" as used herein in connection with MTX means any MTX salt which is pharmaceutically acceptable, that is physically tolerable by the body of a subject treated with it. Preferably, the pharmaceutically acceptable salt of MTX is a sodium salt, a potassium salt, a manganese salt or a calcium salt, or a salt formed from MTX with an organic base such as ammonia. More preferably, the MTX salt is a sodium salt, a potassium salt or an ammonium salt, most preferably a sodium salt. The aforementioned MTX salts preferably contain two of the indicated counterions, that is, both carboxylic acid groups of MTX exist in the form of carboxylate groups, which counter-ion is one of the above indicated ones.

The term "hydrate thereof" means MTX or a salt thereof further comprising water bound to the MTX molecules by non-covalent intermolecular forces. The amount of water comprised in the MTX hydrate or MTX salt hydrate may be non-stoichiometric or stoichiometric.

The phrase "two subsequent sequential time periods" as used in connection with the treatment time means that the time periods are "sequential" in that one time period follows the other, wherein the term "subsequent" defines that the time periods follow one another in the order indicated by their numbering: The treatment time starts with the first time period, thereafter the second time period follows. Optionally, a third time period follows. However, since the treatment time comprises the aforementioned first, second and third time period, it is understood that before, after or between the time periods, there may be optional further time periods. However, preferably, these further time periods also comply with the proviso that the dose of MTX, a pharmaceutically acceptable salt thereof, or a hydrate thereof, is administered at a dose which is decreased within the treatment time comprising the at least three subsequent sequential time periods. More preferably, the treatment time starts with the first time period defined in claim 1, and it ends with the second or third time period, wherein optional further time periods are between the first and second time period, and/or optionally between the second and third time period.

The term "week" as used herein in relation with the at least two or three subsequent sequential time periods means a time period of 7 days, that is 168 hours.

The term "total treatment time" means the treatment time comprising all time periods in which a dose of MTX, a pharmaceutically acceptable salt thereof, or a hydrate thereof, is administered, that is the first, second and third time period and optional further time periods. Preferably, the beginning of the first treatment period is the starting point of the total treatment time, and the end of the second or third treatment time is the end point of the total treatment time.

The term "average dose" as used herein in connection with the MTX, a pharmaceutically acceptable salt thereof, or a hydrate thereof administered within the total treatment time means the arithmetic mean value of the doses administered within said total treatment time on average per week.

Up to now, there was the existing technical prejudice that a relatively high MTX dosing of e.g. about 50 mg/week should be avoided due to tolerability problems of a patient in terms of adverse events (AE). Now, the present inventors overcame this technical prejudice. Namely, they found that MTX dosing can be started with a relatively high dose of e.g. about 50 mg or even more, and then be stepwise decreased. However, the stepwise decrease alone is not the only feature decisive for the aforementioned surprising effect. Rather, in combination with the stepwise decrease, attention has to be paid in particular to the average dose of MTX, a pharmaceutically acceptable salt thereof, or a hydrate thereof, administered to a patient during the total treatment time.

The high efficacy of the present medical use of MTX, a pharmaceutically acceptable salt thereof, or a hydrate thereof, is among others supported by the experimental data illustrated in FIGS. 1 and 2.

BRIEF DESCRIPTION OF THE FIGURES

In FIGS. 1 and 2, W0, W2, W4, W8 and W12 mean week 0, 2, 4, 8 and 12 of the treatment time. The abbreviation "Pt" means patient, so Pt 1 means patient number 1, Pt 2 means patient number 2, and so on. That is, each line plotted within the diagram illustrates the individual change in DAS28 (cf. FIG. 1) and HAQ (cf. FIG. 2) of each patient.

FIGS. 1 and 2 illustrate the high efficacy of the present medical use of MTX and pharmaceutically acceptable salt thereof, namely that in the present experimental examples, at week 12, out of nine, four patients (44.4%) achieved DAS28 remission, two (22.2%) reached low disease activity, one (11.1%) patient showed moderate disease activity, and two (22.2%) had still had high disease activity. In conclusion, 8 out of 9 patients (88.8%) showed a reduction in DAS28>1.2 from baseline. The objective results obtained by the DAS28 value are further confirmed by the more subjective results of the HAS values depicted in FIG. 2, which HAS values in general correlate well with the results of the DAS28 test.

Figure 1:
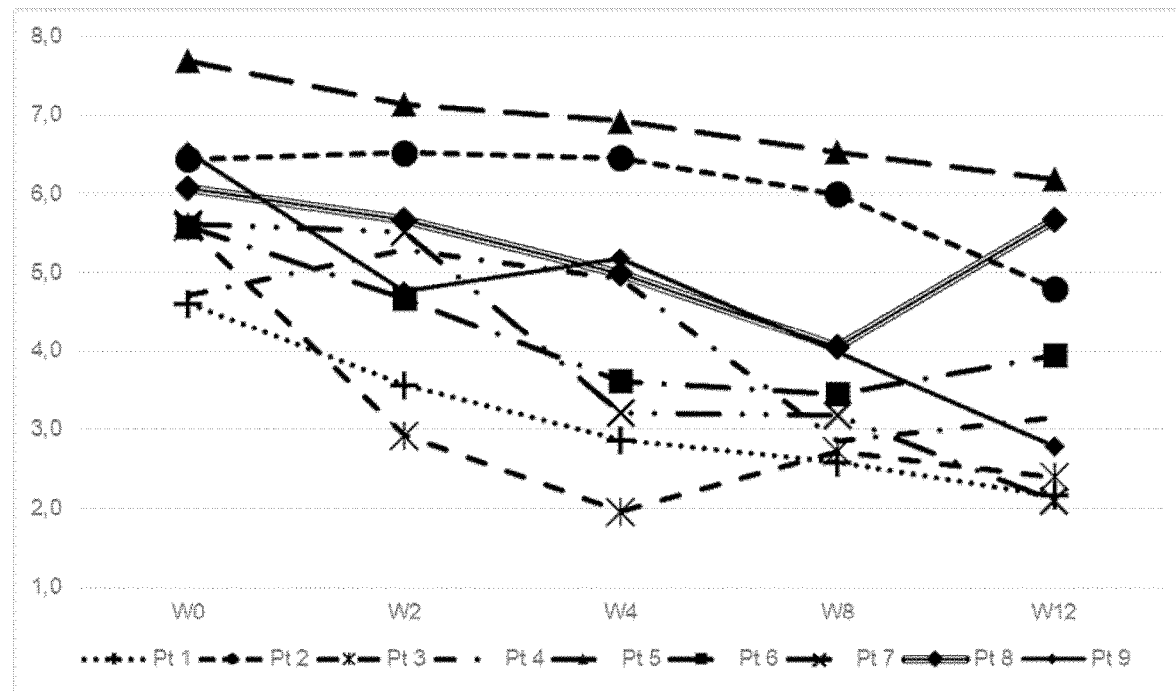
FIG. 1 shows a diagram illustrating the change in disease activity score based on 28 joints (DAS28) from baseline to week 12, in which diagram the x-axis refers to the treatment time in weeks, and the y-axis refers to the DAS28 value.

The average dose of methotrexate or a pharmaceutically acceptable salt administered within the total treatment time depends on the age, height and weight of the patient to be treated, as well as on the severity of the patient's disease. Preferably, the average dose of methotrexate or a pharmaceutically acceptable salt administered within the total treatment time is preferably 27 to 36 mg/week, and more preferably 28 to 32 mg/week.

It is preferred that in the present medical use of MTX, a pharmaceutically acceptable salt thereof, or a hydrate thereof, the dosage regime for administering a dose of methotrexate, a pharmaceutically acceptable salt or a hydrate thereof is as follows:
  i) within the first time period, the dose is preferably 42 to 80 mg/week, more preferably 44 to 70 mg/week, and most preferably 46 to 60 mg/week;
  ii) within the second time period, the dose is preferably 23 to 34 mg/week, and more preferably 24 to 28 mg/week; and
  iii) within the third time period, the dose is preferably 10 to 20 mg/week, more preferably 12 to 20 mg/week, even more preferably 13 to 20 mg/week, and most preferably 14 to 20 mg/week.

Preferably, the doses indicated under items i) to iii) above given in mg/week are respectively administered in the form of a single dose or multiple doses following in relatively direct succession, i.e. within a relatively short time period of e.g. 1 to 15 min, most preferably as a single dose.

For the above described dosage regime, it is preferred that within the first time period, the dose is 38 mg/week to 70 mg/week; within the second time period, the dose is 23 mg/week to 34 mg/week; and within the third time period, the dose is 10 mg/week to 20 mg/week, with the proviso that in the third time period, the dose is decreased compared to the dose in the second time period. More preferably, for the above described dosage regime, within the first time period, the dose is 42 mg/week to 60 mg/week; within the second time period, the dose is 23 mg/week to 28 mg/week; and within the third time period, the dose is 12 mg/week to 20 mg/week.

The first, second and third time period are respectively characterized by at least one of the following features a), b) and c):
  a) the duration of each of the first, second and third time period preferably at least three weeks, even more preferably at least four weeks, most preferably four weeks;
  b) the first, second and third time period have the same duration;
  c) the total treatment time is a time period of 6 to 24 weeks, preferably 9 to 21 weeks, more preferably 12 to 18 weeks, and most preferably 12 weeks.

The term "subsequently follow in direct succession" as used in connection of aforementioned feature c) means that there is no discontinued MTX dosage. That is, there is no time period of one week or more in which no MTX, a pharmaceutically acceptable salt thereof, or a hydrate thereof, is administered. This is a big difference compared with Gabriel S., et al., "*Treatment of rheumatoid arthritis with higher dose intravenous methotrexate*", J. Rheumatol, 1990, 17, pages 460 to 465 disclosing MTX IV dosage which was discontinued due to patient's tolerability problems.

Preferably, methotrexate, a pharmaceutically acceptable salt thereof, or a hydrate thereof, are for use in the treatment of rheumatic and/or inflammatory diseases. More preferably, the rheumatic and/or inflammatory diseases are selected from the group consisting of rheumatoid arthritis, juvenile idiopathic arthritis, joint arthroses, multiple Sclerosis, Crohn's disease, vasculitis, collagenosis, colitis ulcerosa, bronchial asthma, psoriasis, psoriatic arthritis, Alzheimer's disease, Bechterew's disease, systemic lupus erythematosus, systemic sclerosis (scleroderma), polymyositis-dermatomyositis, myasthenia gravis, uveitis, Churg-Strauss Syndrome, Boeck's disease, ankylosing spondylitis, recurrent polychondritis, ulcerative colitis, polymyalgia rheumatica and Giant-cell arteritis; preferably rheumatic arthritis, juvenile idiopathic arthritis, psoriasis and psoriatic arthritis; more preferably rheumatic arthritis and juvenile idiopathic arthritis; and most preferably rheumatic arthritis. In particular, it was experimentally shown by the present inventors that the present medical use of MTX and pharmaceutically acceptable salt thereof is highly efficient in the treatment of rheumatic arthritis, with significantly reduced adverse effects compared with conventional MTX treatments. Without wishing to be bound to theory, it is believed that the present experimental results allow to extrapolate an improved efficiency also for the further rheumatic diseases listed above, in particular juvenile idiopathic arthritis and psoriatic arthritis.

The methotrexate, a pharmaceutically acceptable salt thereof, or a hydrate thereof, may be administered by or is for administration by any known administration route with any pharmaceutical composition suitable for the selected administration route. It is administered subcutaneous, however, alternatively or additionally it may also be administered intramuscular, intravenous or oral.

In particular, then subcutaneously administered, then this may be done by means of any kind of pharmaceutical composition suitable for this kind of administration route. For the dosage regime according to the present medical use, subcutaneous administration is particularly preferred, since the pharmacokinetics of subcutaneous administration are superior to other administration routes, such as intravenous or oral administration. It was surprisingly found by the present inventors that although subcutaneous administration has superior pharmacokinetics, it was well tolerated by the test patients in that there were only negligible adverse effects. By contrast, with conventional MTX therapies, there was the existing technical prejudice that a relatively high MTX dosing should be avoided due to a large extent and amount of adverse events. Now, with the present invention, it is all the more surprising that there are negligible adverse effects when applying MTX by means of the highly effective subcutaneous administration route.

According to the invention, methotrexate or a pharmaceutically acceptable salt is subcutaneously administered in the form of a fluid composition comprising water having at least one of the following features:
- the water is tab water, distilled water, osmosis water, reverse osmosis water or a mixture thereof;
- the water contains a physiological acceptable inorganic salt, preferably sodium chloride;
- the water contains a physiological acceptable inorganic salt in an amount of 6 to 12 g/l, most preferably 8 to 10 g/l.

In addition to the above indicated components, the fluid composition for subcutaneous administration may comprise one or more further pharmaceutically acceptable excipient. The term "pharmaceutically acceptable excipient" as used herein means any physiologically inert, pharmacologically inactive material known in the art being compatible with the physical and chemical characteristics of the present pharmaceutically active agent MTX. Preferred pharmaceutically-acceptable excipients include, but are not limited to, solvents, buffer systems, surfactants, dyes or pigments, and preservatives.

In the aforementioned fluid composition, the methotrexate or pharmaceutically acceptable salt thereof is preferably comprised in a concentration of at least 10 mg/ml, more preferably 13 to 120 mg/ml, even more preferably 14 to 60 mg/ml, and most preferably 15 to 30 mg/ml. In particular, relatively high concentrations of MTX, a pharmaceutically acceptable salt thereof, or a hydrate thereof, are desirable, because with a high concentration, the dose can be administered to the patient by injecting only one syringe instead of two or more.

In the present medical use of methotrexate, a pharmaceutically acceptable salt thereof, or a hydrate thereof, in addition to methotrexate, folinic acid is administered, and preferably, folinic acid is administered orally. The administration of folinic acid in order to significantly reduce or even completely avoid adverse effects in a patient's body. In this connection, it is noted that adverse effects strongly depend on the different tolerability of different patients. Therefore, for patients having a good tolerability towards MTX, a pharmaceutically acceptable salt thereof, or a hydrate thereof, it can be dispensed with administration of folinic acid.

If folinic acid is administered, then is preferred that the folinic acid is administered at a dose at least 6 mg, preferably at least 8 mg, more preferably 9 to 20 mg, even more preferably 10 to 16 mg, most preferably 11 to 13 mg. In the present experimental examples, it was surprisingly found that a dose of about 12 mg of folinic acid is particularly suitable.

The folinic acid may be administered after the dose of MTX, a pharmaceutically acceptable salt thereof, or a hydrate thereof, is administered. Preferably, folinic acid is administered 3 to 24 hours after the dose of methotrexate, a pharmaceutically acceptable salt thereof, or a hydrate thereof, more preferably 6 to 20 hours, even more preferably after 8 to 16 hours, yet even more preferably after 10 to 14 hours, and the most preferably after 11 to 13 hours.

It is preferred that in the present medical use, besides of the optional administration of folinic acid, no further active pharmaceutic ingredient is administered in combination with MTX.

EXPERIMENTAL EXAMPLES

Methods

Study Design

The STEp-down MEthotrexate Therapy in Rheumatoid Arthritis (STEMETRA) was an open-label, monocentric, pilot study with the primary aim of assessing the safety and the tolerability of high dose subcutaneous (SC)-MTX in patients with RA. The study had a duration of 12 weeks. In view of the exploratory nature of this study, the expected enrolment was of 10 patients. Patients received a SC-MTX commercially available formulation (Reumaflex®, Alfasigma, Italy), dispensed as prefilled syringes of 25 mg, 20 mg, and 15 mg. For reaching the dosage of 50 mg at the beginning of the study, patients injected two SC-MTX 25 mg syringes consecutively.

In the present experimental examples, the Disease Activity Score based on 28 joints (DAS28) testing was carried out according to the protocols described in Fransen J. et al., "*Rheumatoid Arthritis measures: Disease Activity Score (DAS), Disease Activity Score-28 (DAS28), Rapid Assessment of Disease Activity in Rheumatology (RADAR), and Rheumatoid Arthritis Disease Activity Index (RADAI)*", Arthritis Rheum 2003; 49, Suppl 9: pages 214 to 224, as well as described in van der Heijde D. M. et al., "*Development of a disease activity score based on judgment in clinical practice by rheumatologists*", J Rheumatol. 1993 March, 20(3), pages 579 to 581.

In the present experimental examples, the Health Assessment Questionaire (HAQ) testing was carried out according to the protocols described in Ramey Dr. et al. in B. Spilker "*Quality of Life and Pharmacoleconomics in Clinical Trials, 2nd ed, The Health Assessment Questionnaire 1995—Status and Review*", Philadelphia: Lippincott-Raven Pub., 1996, pages 227 to 237, as well as described in Fries J. F. et al., "*Measurement of Patient Outcome in Arthritis. Arthritis and Rheumatism*", 1980, 23, pages 137 to 145.

The protocol treatment schedule comprised administration of SC-MTX 50 mg/week for 4 consecutive weeks, followed by 25 mg/week for 4 weeks, and then 15 mg/week for 4 weeks. All patients received oral supplementation of folinic acid (leucovorin) 12 mg, twelve hours after the injection of SC-MTX. All patients had to be MTX-naïve; previous treatment with other conventional synthetic disease modifying anti-rheumatic drugs (cs)DMARDs was allowed only if they have already been withdrawn, for inefficacy or tolerability, before the baseline visit.

At week 12, patients who have not achieved a DAS28<3.2, could increase SC-MTX again to 20 mg/week (step-up) or could receive a biological disease modifying anti-rheumatic drug bDMARD, according to the treating physician's discretion.

Patients were allowed to receive oral prednisone (PDN) at a maximum dosage of 7.5 mg/day if the dose remained stable in the last month before the baseline visit.

If a patient experience fatigue (with an intensity≥grade 2), he/she could receive a double dose of folinic acid: 12 mg at 12 and 24 hours after SC-MTX, respectively.

The study was approved by a local committee and was conducted according to Good Clinical Practice (GCP) guidelines.

Patients

Eligible patients were≥18 years old affected by rheumatic arthritis (RA), according to the 2010 American College of Pharma/European league against rheumatism (ACR/EULAR) classification criteria[12], naïve to MTX and with an active disease, defined as a value of disease activity score (DAS)28≥3.2, with at least four tender joints and four swollen joints. Main exclusion criteria were: ongoing or previous treatment with bDMARDs, severe anaemia (defined as haemoglobin<8.0 mg/dL), severe thrombocytopenia (defined as platelets count<100,000/mm$^3$), severe leucopoenia or neutropenia (defined as white blood cells count<3,000 mm$^3$ or granulocytes count<1,000 mm$^3$), severe hepatic dysfunction [defined as aspartate aminotransferase (AST) or alanine aminotransferase (ALT)≥times the upper limit of normal(ULN)], renal function impairment (defined as creatinine clearance<40 mL/min), alcohol intake>70 g/week, pregnancy or breastfeeding, ongoing severe infections, previous infection with Hepatitis B (HBV) or Hepatitis C (HCV), positivity of Quantiferon or Mantoux test.

Safety and Efficacy Measures

All the adverse events (AE) occurred during the study and follow-up periods were recorded according to the Common Terminology Criteria for Adverse Events (version 4.0).

During each visit, disease activity score based on 28 joints (DAS28) [with both erythrocytes sedimentation rate (ESR) and C-reactive protein (CRP)], simplified disease activity index (SDAI), clinical disease activity index (CDAI), and the Health Assessment Questionnaire (HAQ) were evaluated and calculated as efficacy measures.

Results

Patients Characteristics

Patients' characteristics are listed in Table 1 below. From Table 1 it is derivable that ten patients were enrolled, eight females and two males, with a median age of 58 (range 42-79). Nine out of 10 patients had a disease duration<12 months. The last patient underwent screening and baseline visit, but withdrew consent before receiving SC-MTX; therefore, the following results refer to the nine patients who received the study drug.

TABLE 1

Demographic, clinical and laboratory characteristic of patients at baseline. N (%): N is the number of test patients to which the respectively indicated characteristic applies, and the percentage value indicated in brackets is the percental portion of these patients within the test group of 10 persons; BMI: Body Mass Index; NSAIDs: non-steroidal anti-inflammatory drugs; RF: rheumatoid factor; ACPA: Anti-citrullinated protein antibodies; HAQ: Health Assessment Questionnaire; DAS28: disease activity score based on 28 joints; VAS: visual analogue scale; CRP: C-reactive protein; AST: Aspartate aminotransferase; ALT: Alanine aminotransferase; GGT: Gamma-glutamyl transpeptidase.

| Characteristic: | N (%) | Mean & standard deviation (SD) |
|---|---|---|
| Age (years) | — | 58.1 (12.1) |
| Female | 7 (77.8%) | — |
| BMI | — | 24.6 (4.17) |
| Patients taking prednisone | 8 (80%) | — |
| Mean daily prednisone dose (mg) | — | 5.1 (2.2) |
| Taking NSAIDs | 4 (40%) | — |
| RF positive | 7 (70%) | — |
| ACPA positive | 6 (60%) | — |
| HAQ | — | 1.5 (0.8) |
| DAS28 | — | 5.9 (1.0) |
| DAS28(CRP) | — | 6.2 (1.3) |
| VAS (mm) | — | 55 (29) |
| CRP (mg/L) | — | |
| AST (U/I) | — | 18 (5) |
| ALT (U/I) | — | 22 (18) |
| GGT (U/I) | — | 26 (12) |
| Haemoglobin (g/dL) | — | 12.6 (1.4) |

Safety

All the nine patients completed the 12-week part of the study. A total of 5 AEs occurred in 4 patients; none of the AEs occurred in the first 4 weeks while the patients were taking SC-MTX 50 mg/week, and none of the AEs was severe. Patient #6 experienced an increase of the alanine aminotransferase (ALT) at week 4 (<2 ULN), which resolved spontaneously; at week 8, liver enzymes were normal. The same patient, at week 8, presented vertigo of moderate intensity, after which the patient decided to discontinue MTX. Patient #7 reported moderate fatigue at week 8, which resolved after the per-protocol increase of folinic acid. Patient #8 presented at week 16, while she was taking 20 mg SC-MTX (per-protocol step-up), a urinary tract infection, which resolved after oral antibiotic therapy. Patient #9 presented low back pain at week 8, which resolved after treatment with nonsteroidal anti-inflammatory drugs (NSAIDs) and a muscle relaxant drug prescribed by its general practitioner.

Efficacy

Figure 2:
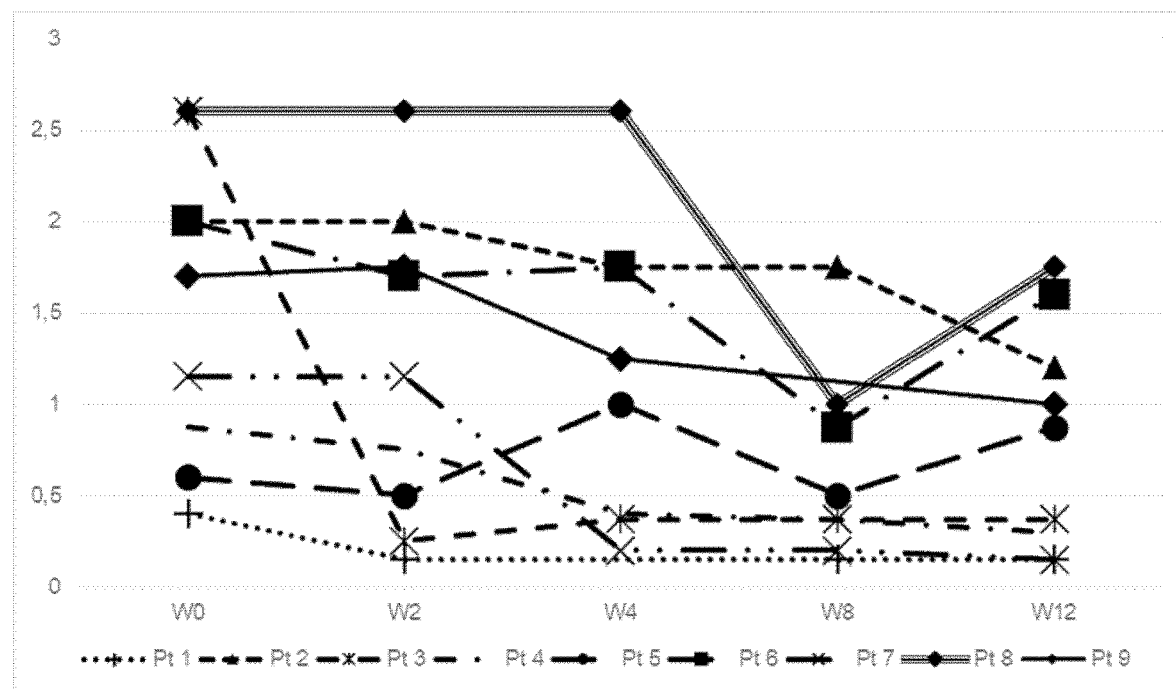
FIG. 2 shows a diagram illustrating the change in a Health Assessment Questionnaire (HAQ) from baseline to week 12, in which diagram the x-axis refers to the treatment time in weeks, and the y-axis refers to the HAQ value.

Changes over time in DAS28 and HAQ are depicted in FIGS. 1 and 2. FIG. 1 shows that at week 12, out of nine, four patients (44.4%) achieved DAS28 remission, two (22.2%) reached low disease activity, one (11.1%) patient showed moderate disease activity, and two (22.2%) had still had high disease activity. Overall, 8 out of 9 patients (88.8%) showed a reduction in DAS28>1.2 from baseline. The objective results obtained by the DAS28 value are further confirmed by the more subjective results of the HAS values depicted in FIG. 2, which HAS values in general correlate well with the results of the DAS28 test, except for the data of patient #5.

Discussion

The results of the above study confirm the good safety profile of MTX, even at a dose significantly higher than applied in prior art treatments. Some of the most feared AEs are cytopenia and liver enzymes elevation, but only one patient presented a mild (and transitory) increase in ALT at week 4. This reassuring safety profile could be the consequence of the supplementation of folinic acid[13]. From the present experimental examples, it is derivable that the underuse of MTX is more related to the concerns of both physicians and patients than to real safety risk. For instance, long-term data suggested that more than 10% of patients could experience liver enzymes elevation, but less than 5% had to stop MTX for that reason[14]. Hence, the present invention overcomes the technical prejudice in the field of medicine that higher doses of MTX, e.g. within a range of 46 to 90 mg/week, do not result in increased AEs. Rather, as derivable from the present experimental examples, such relative high doses were well tolerated by the test persons.

Although the present experiments were carried out with a relative small number of patients and the open-label design of the present experiments, the experiments show that when starting with relative high-doses of SC-MTX and applying the present stepwise, decreasing dosage regime, this resulted in very good efficacy results, with a significant reduction of DAS28 in nearly 90% of the patients. In a recent meta-regression analysis[15], it has been reported that higher doses of MTX did not seem to increase efficacy, however all but one of the included studies used OR-MTX, whose absorption is known to plateau over 15 mg[11].

Therefore, due to the encouraging present experimental results, further experiments will be carried out for confirming the present results by means of a randomized controlled trial.

Conclusion

The present medical use of MTX or a pharmaceutically acceptable salt is an efficacious approach for treating patients e.g. having a rheumatic and/or inflammatory disease such as RA, while patient's tolerability of MTX are good, since there are only few and minor AEs.

REFERENCES CITED IN THE EXPERIMENTAL EXAMPLES

1. Smolen J S, Landewé R, Bijlsma J, Burmester G, Chatzidionysiou K, Dougados M, et al. EULAR recommendations for the management of rheumatoid arthritis with synthetic and biological disease-modifying antirheumatic drugs: 2016 update. Ann Rheum Dis. 2017; 76:960-77.
2. Lopez-Olivo M A, Siddhanamatha H R, Shea B, Tugwell P, Wells G A, Suarez-Almazor M E. Methotrexate for treating rheumatoid arthritis. In: Suarez-Almazor M E, editor. Cochrane Database of Systematic Reviews. Chichester, UK: John Wiley & Sons, Ltd; 2014.
3. Verstappen S M M, Jacobs J W G, van der Veen M J, Heurkens A H M, Schenk Y, ter Borg E J, et al. Intensive treatment with methotrexate in early rheumatoid arthritis: aiming for remission. Computer Assisted Management in Early Rheumatoid Arthritis (CAMERA, an open-label strategy trial). Ann Rheum Dis. 2007; 66:1443-9.
4. Emery P, Sebba A, Huizinga T W J. Biologic and oral disease-modifying antirheumatic drug monotherapy in rheumatoid arthritis. Ann Rheum Dis. 2013; 72:1897-904.
5. Joensuu J T, Aaltonen K J, Aronen P, Sokka T, Puolakka K, Tuompo R, et al. Cost-effectiveness of biologic compared with conventional synthetic disease-modifying antirheumatic drugs in patients with rheumatoid arthritis: a Register study. Rheumatology (Oxford). 2016; 55:1803-11.
6. Dervieux T, Zablocki R, Kremer J. Red blood cell methotrexate polyglutamates emerge as a function of dosage intensity and route of administration during pulse methotrexate therapy in rheumatoid arthritis. Rheumatology (Oxford). 2010; 49:2337-45.
7. Dervieux T, Wessels J A M, van der Straaten T, Penrod N, Moore J H, Guchelaar H-J, et al. Gene-gene interactions in folate and adenosine biosynthesis pathways affect methotrexate efficacy and tolerability in rheumatoid arthritis. Pharmacogenet Genomics. 2009; 19:935-44.
8. Micha R, Imamura F, Wyler von Ballmoos M, Solomon D H, Hernán M A, Ridker P M, et al. Systematic Review and Meta-Analysis of Methotrexate Use and Risk of Cardiovascular Disease. Am J Cardiol. 2011; 108:1362-70.
9. Rohr M K, Mikuls T R, Cohen S B, Thorne J C, O'Dell J R. Underuse of Methotrexate in the Treatment of Rheumatoid Arthritis: A National Analysis of Prescribing Practices in the US. Arthritis Care Res (Hoboken). 2017; 69:794-800.
10. Idolazzi L, Adami S, Capozza R, Bianchi G, Cozzolongo A, Epis O, et al. Suboptimal methotrexate use in rheumatoid arthritis patients in Italy: the MARI study. Clin Exp Rheumatol. 33:895-9.
11. Schiff M H, Jaffe J S, Freundlich B. Head-to-head, randomised, crossover study of oral versus subcutaneous methotrexate in patients with rheumatoid arthritis: drug-exposure limitations of oral methotrexate at doses≥15 mg may be overcome with subcutaneous administration. Ann Rheum Dis. 2014; 73:1549-51.
12. Aletaha D, Neogi T, Silman A J, Funovits J, Felson D T, Bingham C O, et al. 2010 rheumatoid arthritis classification criteria: an American College of Rheumatology/European League Against Rheumatism collaborative initiative. Ann Rheum Dis. 2010; 69:1580-8.
13. Shea B, Swinden M V, Tanjong Ghogomu E, Ortiz Z, Katchamart W, Rader T, et al. Folic acid and folinic acid for reducing side effects in patients receiving methotrexate for rheumatoid arthritis. In: Shea B, editor. Cochrane Database of Systematic Reviews. Chichester, UK: John Wiley & Sons, Ltd; 2013.
14. Salliot C, van der Heijde D. Long-term safety of methotrexate monotherapy in patients with rheumatoid arthritis: a systematic literature research. Ann Rheum Dis. 2009; 68:1100-4.
15. Bergstra S A, Allaart C F, Stijnen T, Landewé R B M. Meta-Regression of a Dose-Response Relationship of Methotrexate in Mono- and Combination Therapy in Disease-Modifying Antirheumatic Drug-Naive Early Rheumatoid Arthritis Patients. Arthritis Care Res (Hoboken). 2017; 69:1473-83.

The invention claimed is:

1. A method for the treatment of a disease comprising the step of subcutaneously administering methotrexate, a pharmaceutically acceptable salt thereof, or a hydrate thereof, characterized in that methotrexate, a pharmaceutically acceptable salt, or a hydrate thereof is subcutaneously administered with a dosage regime being as follows:
   i) within a first time period, the dose is 38 to 80 mg/week;
   ii) within a second time period, the dose is 22 to 34 mg/week; and
   iii) within a third time period, the dose is 8 to 20 mg/week, the duration of each of the first, second and third time period is at least two weeks respectively, and the first, second and third time period subsequently follow in direct succession, with the proviso that within the total treatment time, the average dose of methotrexate, a pharmaceutically acceptable salt thereof, or a hydrate thereof administered is 26 to 40 mg/week, and wherein the disease is selected from the group consisting of rheumatoid arthritis, psoriasis, psoriatic arthritis, and polymyalgia rheumatica.

2. The method according to claim 1, wherein the average dose of methotrexate or a pharmaceutically acceptable salt administered within the total treatment time is 27 to 36 mg/week.

3. The method according to claim 1, wherein a dosage regime for administering the dose of methotrexate, a pharmaceutically acceptable salt or a hydrate thereof is as follows:
  i) within the first time period, the dose is 42 to 80 mg/week;
  ii) within the second time period, the dose is 23 to 34 mg/week; and
  iii) within the third time period, the dose is 10 to 20 mg/week.

4. The method according to claim 3, wherein the first, second and third time period are respectively characterized by at least one of the following features a), b) and c):
  a) the duration of each of the first, second and third time period is preferably at least three weeks;
  b) the first, second and third time period have the same duration;
  c) the total treatment time is a time period of 6 to 24 weeks.

5. The method according to claim 1, wherein the step of subcutaneously administering is carried out in the form of a fluid composition comprising water having at least one of the following features:
  the water is tap water, distilled water, osmosis water, reverse osmosis water or a mixture thereof;
  the water contains a physiological acceptable inorganic salt;
  the water contains a physiological acceptable inorganic salt in an amount of 6 to 12 g/l.

6. The method according to claim 5, wherein in the fluid composition, the methotrexate or pharmaceutically acceptable salt thereof is comprised in a concentration of at least 10 mg/ml.

7. The method according to claim 1, wherein in addition to methotrexate, folinic acid is administered at a dose of at least 6 mg.

8. The method according to claim 7, wherein folinic acid is administered after the dose of methotrexate, a pharmaceutically acceptable salt thereof, or a hydrate thereof, 3 to 24 hours after the dose of methotrexate, a pharmaceutically acceptable salt thereof, or a hydrate thereof.

* * * * *